United States Patent [19]

Catt et al.

[11] Patent Number: 5,037,652

[45] Date of Patent: Aug. 6, 1991

[54] VANCOMYCIN PRECIPITATION PROCESS

[75] Inventors: Harold R. Catt, Brownsburg; Harold B. Hayes, Indianapolis, both of Ind.

[73] Assignee: Eli Lilly and Company, Indianapolis, Ind.

[21] Appl. No.: 315,751

[22] Filed: Feb. 27, 1989

Related U.S. Application Data

[63] Continuation-in-part of Ser. No. 138,735, Dec. 28, 1987, abandoned.

[51] Int. Cl.$^5$ ............................................. A61K 55/74
[52] U.S. Cl. .................................................... 424/123
[58] Field of Search ........................................ 424/123

[56] References Cited

U.S. PATENT DOCUMENTS 3,067,099 12/1962 McCormick et al. ............... 167/65
3,816,618 12/1972 Raun .................................. 424/115
4,440,753 4/1984 McCormick et al. ............... 424/124

FOREIGN PATENT DOCUMENTS 0145484 11/1984 European Pat. Off. .

OTHER PUBLICATIONS

McCormick et al., "Vancomycin, A New Antibiotic. I. Chemical and Biologic Properties", *Antibiotics Annual* 1955–1956, pp. 606–611.

Higgins et al., "Vancomycin, A New Antibiotic. IV. Purification and Properties of Vancomycin", *Antibiotics Annual* 1957–1958, pp. 906–914.

*Primary Examiner*—Jerome D. Goldberg
*Attorney, Agent, or Firm*—William B. Scanlon; Leroy Whitaker

[57] ABSTRACT

This invention provides an improvement in the large scale processing of vancomycin which comprises the quiescent precipitation of vancomycin base from an aqueous solution of a pH of at least about 7.8.

9 Claims, No Drawings

VANCOMYCIN PRECIPITATION PROCESS

CROSS-REFERENCE TO RELATED APPLICATION

This application is a continuation-in-part of application Ser. No. 07/138,735, filed Dec. 28, 1987 now abandoned.

SUMMARY OF THE INVENTION

This invention provides an improvement in the large scale processing of vancomycin which comprises the quiescent precipitation of vancomycin base from an aqueous solution at a pH of at least about 7.8.

BACKGROUND OF THE INVENTION

Vancomycin is a commercially successful antibiotic which has been available since the late 1950's. Vancomycin and a method for its preparation and isolation are described in U.S. Pat. No. 3,067,099. Vancomycin also is described as being useful for improving feed efficiency in ruminants; see U.S. Pat. No. 3,816,618.

Because of the interest in vancomycin and its importance, new and more efficient methods of isolating this antibiotic from its fermentation mixtures are continually sought.

DETAILED DESCRIPTION

Vancomycin is a fermentation product. Conventionally, the fermentation broth is filtered and the filtrate is acidified and passed over one or more chromatographic resins to effect separation of the antibiotic activity. The pH of the eluate containing purified antibiotic activity then is adjusted to between about 8.0 and about 8.2 by addition of base with stirring. Precipitation of vancomycin base generally begins between about pH 7.2 and 7.5, i.e., before the desired pH is reached. The crystal slurry is stirred and the pH continually readjusted to the desired point until precipitation is complete. This procedure gives inconsistent yields, unpredictable precipitation and a precipitate that is irregularly formed and difficult to filter. On a commercial scale, filtration can be achieved in a reasonable time only by using a filter press. The precipitate cannot be separated using a Buchner filter or centrifuge.

The difficulty in filtering slurries of vancomycin base has been a problem in the commercial production of vancomycin for over twenty years. Previous attempts to obtain a product which could easily be separated failed.

It has now been discovered that if precipitation of vancomycin base is delayed until the pH of the solution is at least about 7.8 and precipitation is completed without agitation, large well-formed platelets consistently are produced. These platelets can be readily filtered with a Buchner filter, a centrifuge, or a filter press. In addition, the yield is increased and the improved filterability of the product allows solutions containing a higher concentration of vancomycin to be processed, thus also increasing the yield of vancomycin per batch and improving the efficiency of the process.

The improved process of the present invention comprises rapidly combining an aqueous solution of vancomycin with an aqueous solution of base to give a solution of about pH 7.8 to about pH 9.0 before precipitation begins and allowing precipitation to continue without agitation. The term "about pH 7.8" means the minimum pH at which a quiescent precipitation technique produces well-formed, easily-filtered platelets of vancomycin base. At high concentrations of vancomycin, it is possible that such a precipitate may be formed at a pH as low as about 7.5, if there is no agitation. Under such conditions, however, precipitation is incomplete and yields are reduced. If agitation is continued for very long after precipitation begins, an irregular, hard to filter product is obtained. At pH above about 9.0, the stability of vancomycin is affected and reduced yields and discolored products are obtained. Best results are achieved when precipitation begins at a pH between about 7.8 and about 9.0, preferably between about pH 8.0 and about pH 8.5, and most preferably at about pH 8.2. Preferably, a pH between about 8.0 and about 8.5 is reached and agitation is stopped before precipitation begins.

The term "base" means a compound which yields hydroxyl ions in aqueous solution. Examples of suitable bases include sodium hydroxide, potassium hydroxide, ammonium hydroxide, triethylamine, and the like.

In one embodiment of the invention, the pH of vancomycin eluate concentrate is adjusted to between about pH 6.5 and about pH 7.0 with a base, such as sodium hydroxide. An aliquot is removed and titrated to determine the amount of base necessary to raise the pH to at least about 7.8. The calculated amount of base is added to the eluate concentrate rapidly with agitation to reach a pH of at least about 7.8 before precipitation begins. It may be desirable to add the base to the eluate concentrate under pressure. Agitation is stopped immediately after the base is added and the solution is allowed to stand. Preferably, the base is added at a rate such that a pH between about 8.0 and about 8.5, most preferably about 8.2, is reached and agitation is stopped before precipitation begins. Large, well-formed platelets which are easily filtered are obtained.

In another embodiment of the invention, the pH of eluate concentrate is adjusted to between about 6.5 and about 7.0. The solution is added rapidly with agitation to a solution of base of an appropriate concentration to provide a final pH of at least about 7.8. The solution of base may be buffered. Agitation is stopped immediately following the addition of the eluate concentrate. It is again preferable that the entire volume of eluate is added to the base before precipitation begins and that the final pH is between about 8.0 and about 8.5, most preferably about 8.2. Large, well-formed platelets which are easily filtered are obtained.

The rate of precipitation is affected by the temperature of the solution. Preferably, the solution is maintained at a temperature between about 10° C. and about 30° C. When the temperature of the solution is above about 30° C., precipitation frequently starts before a pH of at least about 7.8 is reached. The resulting vancomycin base is difficult to filter. Conversely, at temperatures below about 10° C., precipitation proceeds slowly and is less than half complete after two hours. Therefore, crystallization preferably is carried out at a temperature between about 10° C. and about 30° C., most preferably between about 20° C. and about 25° C., in order to obtain an easily filtered precipitate within a commercially reasonable time.

The rate of precipitation also is affected by the concentration of vancomycin in the eluate. Preferably, the eluate concentrate contains from about 60 mg/ml to about 200 mg/ml of vancomycin, more preferably between about 75 mg/ml and about 200 mg/ml, and most preferably between about 85 mg/ml and about 160 mg/ml. In general, the higher the concentration, the faster the rate of precipitation and the more complete the precipitation. At the higher concentrations it may be necessary to adjust the pH at a temperature of about 20° C., or lower, to prevent premature precipitation of vancomycin base. The temperature then may be raised to about 25° C. until precipitation is completed. Precipitation of vancomycin base from solutions having concentrations less than about 75 mg/ml occurs more slowly and gives a product which filters more slowly than higher concentrations.

The invention is illustrated by the following examples, which are not to be considered as limiting.

EXAMPLE 1

A 440 ml aliquot of eluate concentrate containing 75 mg/ml vancomycin was adjusted to pH 7.0 by addition of 3N sodium hydroxide with stirring. The pH was further adjusted from pH 7.0 to pH 8.24 by the addition of 3N sodium hydroxide in 75 seconds. Stirring was stopped immediately following addition of the sodium hydroxide. Vancomycin base began precipitating after 1.5 min. The temperature of the solution was maintained at 25° C. The rate of crystallization was followed by ultraviolet assay. After about 6 hours the slurry was filtered on a 1.25-inch diameter Buchner plate, fitted in a glass column, at 14 psi. The filter cake was washed with 105 ml of 50% aqueous ethanol followed by a second wash with 105 ml of methanol. The filtration times were 7.5 min., first wash 11.0 min., and second wash 9.0 min. The yield of vancomycin base was 90.0%.

EXAMPLES 2-5

The procedure of Example 1 was repeated using eluate concentrates containing 90, 120, and 160 mg/ml. Precipitation from a 160 mg/ml solution was carried out twice. During the first experiment at a controlled temperature of 25° C., precipitation began at pH 7.9. Stirring was stopped when the entire aliquot of sodium hydroxide was added and the pH was 8.24. In the second experiment, the eluate was at 10° C. and the sodium hydroxide solution at 15° C., which gave a crystallization temperature of 21° C. Stirring was stopped immediately after addition of the sodium hydroxide, pH 8.23. Precipitation began 35-40 seconds later.

The results of Examples 1 to 5 are summarized in Table 1.

TABLE 1

| | % Vancomycin Crystallized | | | | |
|---|---|---|---|---|---|
| | Ex 1 | Ex 2 | Ex 3 | Ex 4 | Ex 5 |
| | Vancomycin Concentration, mg/ml | | | | |
| | 75 | 90 | 120 | 160* | 160 (Cold) |
| Time | | | | | |
| 30 min. | | 62.0 | 87.4 | 95.9 | |
| 45 min. | 63.6 | | | | 92.9 |
| 60 min. | 82.5 | 82.5 | 92.4 | 96.2 | 92.8 |
| 90 min. | 84.1 | 85.8 | | | 94.6 |
| 105 min. | | | 94.5 | | |
| 120 min. | 84.8 | 88.1 | 94.9 | | |
| 150 min. | 86.0 | 90.3 | 95.6 | | |
| 180 min. | 88.5 | | | | 95.4 |
| 210 min. | 88.7 | 92.4 | | | |
| 300 min. | 90.0 | | | | |

*Precipitation began at pH 7.9.

| Filtration time | | | | | |
|---|---|---|---|---|---|
| Filtration, min. | 7.5 | 3.7 | 1.2 | 3.1 | 0.9 |
| 1st wash, min. | 11.0 | 5.9 | 2.3 | 7.6 | 1.6 |
| 2nd wash, min. | 9.0 | 5.9 | 2.8 | 8.3 | 1.3 |
| Total | 27.5 | 15.5 | 6.3 | 19.0 | 3.8 |

EXAMPLES 6-9

The procedure of Example 1 was repeated using an eluate concentration of 83.7 mg/ml, but varying the temperature. The results are summarized in Table 2. In Example 9 at 30° C., precipitation began before all of the sodium hydroxide was added.

TABLE 2

| | % Vancomycin Crystallized | | | |
|---|---|---|---|---|
| | Ex 6 | Ex 7 | Ex 8 | Ex 9 |
| | Temperature | | | |
| Time | 5° C. | 20° C. | 25° C. | 30° C. |
| 30 min. | 12.7 | 11.2 | 51.1 | 94.4 |
| 60 min. | 26.1 | 22.2 | 73.3 | 94.3 |
| 90 min. | 35.7 | 37.5 | 83.9 | 95.3 |
| 120 min. | 35.9 | 42.4 | 85.6 | |
| 150 min. | 38.2 | 49.3 | 86.7 | |
| 180 min. | | 57.1 | 86.8 | |
| 270 min. | | 73.5 | | |
| 360 min. | | 78.3 | | |

EXAMPLE 10

Urea (14.8 g) was added to a 200 ml aliquot of eluate concentrate containing 74 mg/ml of vancomycin. The pH was adjusted to pH 6.5 with 33 ml of 3N sodium hydroxide. The solution was added in 10-15 seconds with stirring to 30 ml of 3N sodium hydroxide containing 2.5 g of sodium acetate and the stirring immediately stopped. The pH was 8.0. The temperature of the solution was maintained at 25° C. Precipitation of vancomycin base began immediately. After 30 min. the slurry was filtered on a 9 cm diameter Buchner. The filter cake was washed with 100 ml of 50% aqueous methanol followed by a second wash with 100 ml methanol. Filtration times were 1.9 min., first wash 2.6 min., and second wash 2.6 min. The yield was 95.0%.

EXAMPLES 11-14

The procedure of Example 10 was repeated using varying amounts of urea and sodium acetate. In some cases, the second wash was with methanol and a third wash with acetone was added.

As a control, 200 ml of a crystal slurry prepared by the prior art method from eluate containing 73 mg/ml vancomycin was filtered on a 9 cm Buchner.

The results of Examples 10-14 are summarized in Table 3.

TABLE 3

| | Filtration Times | | | | |
|---|---|---|---|---|---|
| | Ex 10 | Ex 11 | Ex 12 | Ex 13 | Ex 14 Control |
| Urea, g | 14.8 | 14.8 | none | none | |
| Sodium acetate, g | 2.5 | 2.0 | 2.0 | none | |
| Washes 1 | 50% MeOH | MeOH | 50% MeOH | 50% MeOH | 50% MeOH |
| 2 | MeOH | MeOH | MeOH | MeOH | MeOH |

TABLE 3-continued

|  | Filtration Times | | | | |
| --- | --- | --- | --- | --- | --- |
|  | Ex 10 | Ex 11 | Ex 12 | Ex 13 | Ex 14 Control |
| 3 |  |  | Acetone |  | Acetone |
| Filtration, min. | 1.9 | 1.6 | 1.5 | 0.75 | 10.7 |
| 1st wash, min. | 2.6 | 1.6 | 1.25 | 0.67 | 21.8 |
| 2nd wash, min. | 2.6 | 1.5 | 0.35 | 0.43 | 11.0 |
| 3rd wash, min. |  |  | 0.25 |  | 2.0 |
| Total | 7.1 | 4.7 | 3.35 | 1.85 | 45.5 |
| Yield, % | 95.2 | 91.4 | 89.2 | 91.7 | ~85 |

TABLE 4

|  | Filtration Times | | |
| --- | --- | --- | --- |
|  | Ex. 15 | Ex 16 | Ex. 17 Control (average) |
| Filtration, min. | 10 | 8 | 20 |
| 1st wash, min. | 15 | 13 | 80 |
| 2nd wash, min. | 7 | 8 | 150 |
| Total | 32 | 29 | 250 |
| Yield, % | 92 | 92 | ~85 |

EXAMPLE 15

The pH of 750 l of eluate concentrate at 15° C. containing 85 mg/ml vancomycin was adjusted to pH 7.0 by addition of sodium hydroxide at 19° C. An aliquot was titrated to pH 8.2 and the amount of 3N sodium hydroxide necessary to raise the pH of the eluate to pH 8.2 was calculated. This amount, 56 l, was added to a pressure pot and blown into the tank in 2.5 min. and stirring was stopped. Precipitation began before all of the sodium hydroxide was added. The temperature of the solution was stabilized at 25° C. After 4.5 hours the slurry was filtered on a filter press. The filter cake was washed with water until the conductivity was less than 3000 μmho (about 1300 l), followed by a second wash with 950 l acetone. The filtration times were 10 min.; first wash 15 min; and second wash 7 min. The yield was 92%.

EXAMPLES 16–17

The procedure of Example 15 was repeated, except that the sodium hydroxide was added in 1.5 min. and precipitation began 15 seconds after the addition was completed.

The results of Examples 15 and 16 were compared with the average filtration times of the previous three standard production runs using the prior art method with eluate containing 75±15 mg/ml vancomycin.

The results of Examples 15–17 are summarized in Table 4.

We claim:

1. A process for crystallizing vancomycin base which comprises rapidly combining an aqueous solution containing from about 60 mg/ml to about 100 mg/ml of vancomycin with an aqueous solution of a base selected from sodium hydroxide, potassium hydroxide or ammonium hydroxide at a temperature between about 10° C. and about 30° C. to give a solution of about pH 7.8 to about pH 9.0 before crystallization begins and allowing crystallization to continue without agitation.

2. The process of claim 1 wherein the pH is between about 8.0 and about 8.5.

3. The process of claim 1 wherein the pH is about 8.2.

4. The process of claim 1 wherein a pH between about 8.0 and 8.5 is reached and agitation is stopped before crystallization beings.

5. The process of claim 4 wherein the pH is about 8.2.

6. The process of claim 1 wherein the aqueous solution of vancomycin contains from about 75 mg/ml to about 200 mg/ml vancomycin.

7. The process of claim 6 wherein the aqueous solution of vancomycin contains from about 85 mg/ml to about 160 mg/ml vancomycin.

8. The process of claim 1 wherein the solution is maintained at a temperature between about 20° C. and about 25° C.

9. The process of claim 1 wherein the base is sodium hydroxide.

* * * * *

UNITED STATES PATENT AND TRADEMARK OFFICE
CERTIFICATE OF CORRECTION

PATENT NO. : 5,037,652
DATED : August 6, 1991
INVENTOR(S) : Harold R. Catt et al.

It is certified that error appears in the above-identified patent and that said Letters Patent is hereby corrected as shown below:

Column 6, line 26, "100 mg/ml" should read -- 200 mg/ml -- .

Signed and Sealed this

Thirtieth Day of June, 1998

Attest:

BRUCE LEHMAN

Attesting Officer    Commissioner of Patents and Trademarks